(12) United States Patent
Strauss et al.

(10) Patent No.: US 8,119,084 B2
(45) Date of Patent: Feb. 21, 2012

(54) REACTOR FOR ISOPARAFFIN OLEFIN ALKYLATION

(75) Inventors: Ramon A. Strauss, Herndon, VA (US); Ramesh R. Hemrajani, Millington, NJ (US); Guido L. Spinelli, Toronto (CA)

(73) Assignee: ExxonMobil Research & Engineering Company, Annandale, NJ (US)

( * ) Notice: Subject to any disclaimer, the term of this patent is extended or adjusted under 35 U.S.C. 154(b) by 503 days.

(21) Appl. No.: 12/380,098

(22) Filed: Feb. 24, 2009

(65) Prior Publication Data

US 2009/0287033 A1 Nov. 19, 2009

Related U.S. Application Data

(60) Provisional application No. 61/071,773, filed on May 16, 2008.

(51) Int. Cl.
*B01J 19/00* (2006.01)
*B01J 19/18* (2006.01)

(52) U.S. Cl. .................. 422/630; 422/225; 422/228

(58) Field of Classification Search .......... 422/630, 422/225, 228
See application file for complete search history.

(56) References Cited

U.S. PATENT DOCUMENTS

| | | | |
|---|---|---|---|
| 2,379,368 A | 6/1945 | Matuszak | |
| 2,429,205 A | 10/1947 | Jenny et al. | |
| 2,438,852 A * | 3/1948 | Goldsby et al. | 585/706 |
| 2,463,262 A | 3/1949 | Goldsby | |
| 2,768,987 A | 10/1956 | Hart | |
| 2,775,636 A * | 12/1956 | Rupp | 585/720 |
| 2,852,581 A | 9/1958 | Stiles | |
| 2,859,259 A | 11/1958 | Stiles | |
| 2,903,344 A | 9/1959 | Rollman et al. | |
| 2,920,124 A | 1/1960 | Stiles et al. | |
| 3,170,002 A | 2/1965 | Kelso | |
| 3,837,812 A * | 9/1974 | Boontje | 422/245.1 |
| 3,982,903 A | 9/1976 | Anderson | |
| 4,075,258 A | 2/1978 | Caulk et al. | |
| 4,293,729 A | 10/1981 | Kolb et al. | |
| 5,785,933 A | 7/1998 | Cunningham et al. | |

FOREIGN PATENT DOCUMENTS

| | | |
|---|---|---|
| WO | WO 99/48845 | 9/1999 |
| WO | WO 01/94283 | 12/2001 |

OTHER PUBLICATIONS

International Search Report, PCT/US2009/002928, mailed Jul. 20, 2009.
Written Opinion, PCT/US2009/002928, mailed Jul. 20, 2009.

* cited by examiner

*Primary Examiner* — Jennifer A Leung
(74) *Attorney, Agent, or Firm* — Malcolm D. Keen; Glenn T. Barrett

(57) ABSTRACT

A reactor for the autorefrigerant alkylation process has a cylindrical upright reactor vessel with the inlet for the refrigerant reactant and the sulfuric acid at its lower end and a series of inlets for the olefin reactant at vertically spaced intervals up the length of the reactor. An extended, sinuous flow path for the reactants is provided by means co-acting baffles co-acting baffles having, alternately along the length of the reactor, central flow passages and peripheral flow passages for the reaction mixture to define sequential reaction zones in which alkylation takes place. The baffles interact with a rotary mixer with multiple impellers located on the reactor axis. The reaction mixture flows alternately towards and away from the reactor walls in the sequence of serial reaction zones within the reactor to promote mixing of the isoparaffin reactant with the acid catalyst.

7 Claims, 2 Drawing Sheets

REACTOR FOR ISOPARAFFIN OLEFIN ALKYLATION

CROSS REFERENCE TO RELATED APPLICATIONS

Figure 1:
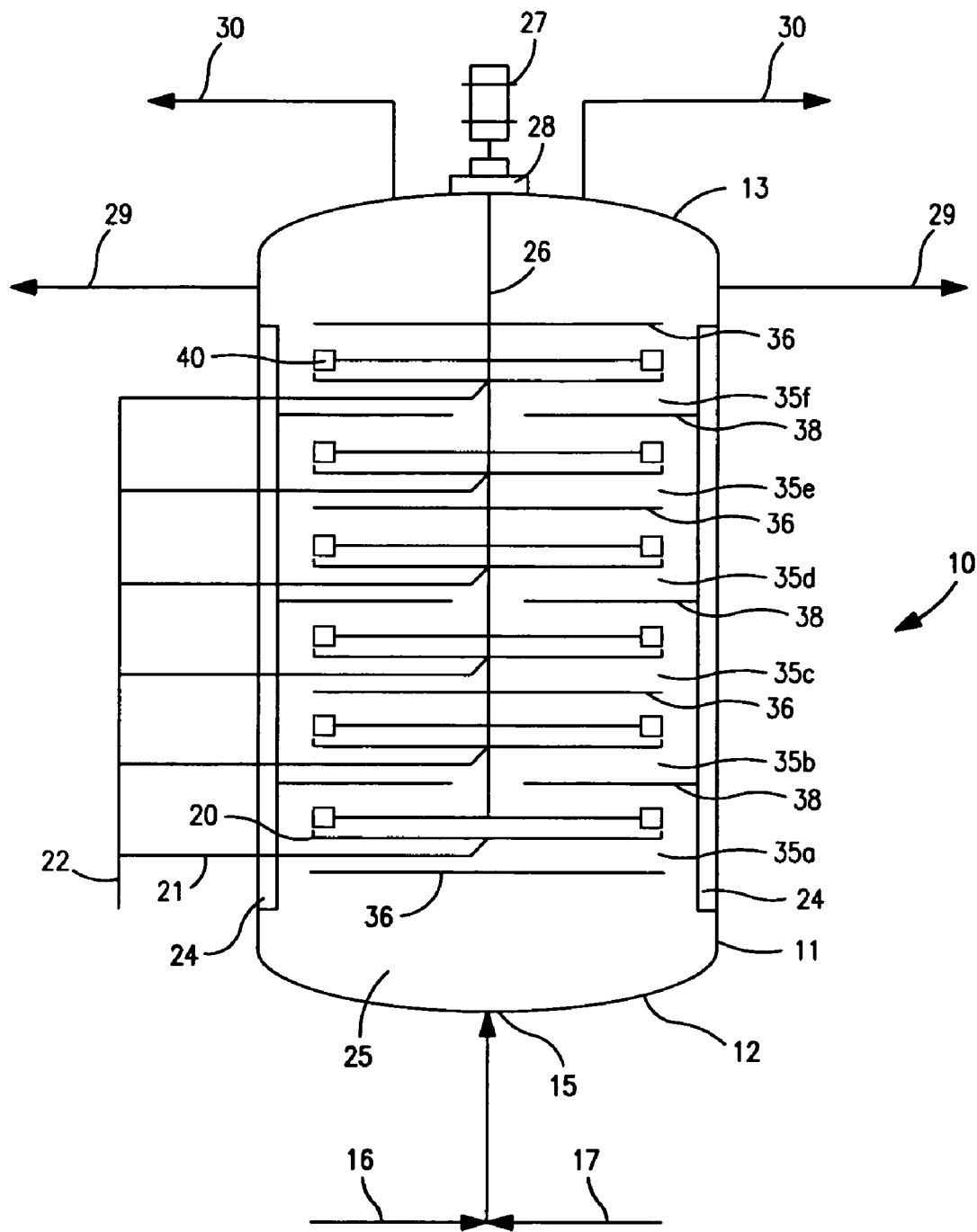

This application claims priority from U.S. application Ser. No. 61/071,773, filed 16 May 2008.

FIELD OF THE INVENTION

This invention relates to a reactor which is useful in the isoparaffin-olefin alkylation reaction and, more particularly, to a reactor which is useful for the sulfuric acid catalyzed isoparaffin-olefin alkylation process.

BACKGROUND OF THE INVENTION

One of the common petroleum refinery processes for the upgrading of light ends to high octane gasoline is the isoparaffin-olefin alkylation process in which an isoparaffin, usually isobutene is alkylated with a light olefin, usually propylene, butene or mixtures of the two, to produce a high octane liquid product in the gasoline boiling range. The alkylate product is considered a premium gasoline blending component due to its high octane, low RVP, low sulfur content and low distillation T90 point. Two major isoparaffin-olefin alkylation process have become widely accepted in the refining industry, the sulfuric acid process and the hydrofluoric acid (HF) process which, while fundamentally similar, possess different characteristics arising from the different abilities of the two acids to catalyze the alkylation reaction. These two processes are by now well established in the refining industry and each is recognized as having its own technical and economic advantages and problems.

Current worldwide gasoline demand, along with more stringent environmental limitations, are driving refineries to expand and consider new alkylation units. While the process economics may in many cases favor the HF process, economics alone may not always be the determining factor and sulfuric acid alkylation has retained a major portion of the alkylation capacity in the industry. Many of the new projects are likely to choose sulfuric acid as catalyst as a result of perceptions concerning the safety and environmental concerns about HF alkylation in spite of its excellent plant safety and environmental record. Solid acid catalyst technology, while attractive in principle, is, however, quite far from being sufficiently well established for widespread commercial acceptance, leaving sulfuric acid as a currently viable option, in spite of reactor reliability issues, especially with rotating equipment and internals.

There are two major variants of the sulfuric acid alkylation process which differ principally in the means used to remove the heat of the alkylation reaction. The DuPont™ Stratco™ process, the dominant process also known as the effluent refrigeration process, uses a liquid full reactor/acid settler system in which the heat of reaction is removed by an internal tube bundle, making the reactor resemble a shell-and-tube type heat exchanger although with an agitator which is used to secure good contact between the acid and the hydrocarbon reactants. Control of the pressure in the flash drum maintains the contents of the reactor in the liquid phase at by appropriate control, the temperature of the reactant mixture is kept at a desired value. The autorefrigerant process pioneered by Esso (now ExxonMobil), by contrast, uses a reactor in which the heat of reaction is removed by operation at a pressure at which a portion of the hydrocarbon charge boils. The reactor used in the autorefrigerant process conventionally comprises a single horizontal vessel divided into mixing chambers with one to two separate pressure zones. Plug flow is achieved by cascade operation with the refrigerant and sulfuric acid being admitted at one end of the contactor and the olefin being introduced progressively in the mixing chambers by means of spargers with vigorous mixing provided by driven impellers or, in certain cases, eductor type mixers. The reactant mixture and acid catalyst passes from chamber to chamber over weirs and through a pressure let down between the two pressure zones. Vaporization of the refrigerant removes the heat of reaction and very low temperatures can be achieved while operating at low pressure.

Considering the available options for sulfuric acid alkylation, the main technical disadvantages of the Stratco contactor can be summarized as the following:

Liquid phase operation requires higher pressure than autorefrigerated reactors and therefore it operates at a higher temperature which promotes secondary reactions.

The hydrodynamics in the contactor consist of high velocity pumping of liquid by the single mixer required to create high liquid velocities over the heat exchanger tubes. As a result, the emulsion is subjected to very high energy dissipation locally in the region of the mixer blades and low energy dissipation everywhere else.

The compressor energy requirement is between 15 and 20% higher than with autorefrigerated systems.

The capacity of a contactor is typically 1200 to 2000 BPD (about 1900-3200 hl/day) of alkylate. Therefore, a typical unit will require between 5 and 8 reactors. Each reactor needs its own settler, pumps, and control system.

With the autorefrigerant process, most units require only one reactor and settler. However, there are some disadvantages:

Vessels can get very large: 12-15 ft (about 3.6-4.5 m.) diameter and over 100 ft (about 30 m.) in length.

Long residence times affect alkylate quality due to alkylate decomposition reactions.

Multiple mixing zones require multiple mixers, motors, and gearboxes which has an effect on maintenance and reliability control resources.

The horizontal configuration is considered less efficient in terms of volume utilization.

The large sizes make it less competitive for units smaller than 10 kBD (about 15900 hl/Day) whereas many refineries will normally be satisfied by a capacity of 5-10 kBD (about 8000-16000 hl/day).

Given the continued viability of the autorefrigerant sulfuric acid alkylation process, it would be desirable to incorporate improvements which negate or offset at least some of the disadvantages mentioned above.

The present invention is concerned with improvements to the autorefrigerant alkylation process. Accordingly, in this specification, the term "alkylation" is used to refer to the isoparaffin-olefin alkylation process of the petroleum refining industry in which a light olefin ($C_2$-$C_6$, usually $C_3$-$C_4$) is used to alkylate a light isoparaffin ($C_4$-$C_6$, usually isobutane) to produce a liquid alkylation product which is predominantly in the gasoline boiling range. The autorefrigerant alkylation process, referred to as such in this specification is the alkylation process in which heat of the alkylation reaction is removed by vaporization of a reactant hydrocarbon refrigerant. Exemplary patents describing variants of the autorefrigeration alkylation process include U.S. Pat. No. 2,429,205 (Jenny); U.S. Pat. No. 2,768,987 (Hart); U.S. Pat. No. 2,903,344 (Rollman); U.S. Pat. No. 3,170,002 (Kelso); U.S. Pat.

No. 2,852,581 (Stiles); U.S. Pat. No. 2,859,259 (Stiles) and U.S. Pat. No. 2,920,124 (Stiles).

SUMMARY OF THE INVENTION

According to the present invention, an improved reactor is provided for the autorefrigerant alkylation process. The reactor, which operates in the same fundamental manner as the conventional autorefrigerated reactor with three phases, acid liquid, hydrocarbon liquid and hydrocarbon vapor, is characterized by a upright, closed, generally cylindrical reactor vessel disposed with an inlet or inlets for the refrigerant reactant and the sulfuric acid at its lower end and a series of inlets for the olefin reactant at vertically spaced intervals up the length of the reactor. An extended flow path for the reactants is provided by means co-acting baffles which define sequential reaction zones in which alkylation takes place with the reaction mixture of isoparaffin, olefin and catalyst following an extended, sinuous or serpentine flow path as it ascends the reactor. The baffles interact with a rotary mixer with multiple impellers located on the reactor axis which provides agitation to the mixture ascending the reactor additional to that created by the ebullition of the refrigerant. An outlet or outlets for the vaporized refrigerant and the reaction effluent are provided at the upper end of the vessel.

Notable advantages of the reactor and of the autorefrigerant process operate in the improved reactor are:
 The vertical vessel design is more consistent with current reaction engineering technology.
 Efficient volume utilization ensures a fast alkylation reaction while limiting unwanted secondary reactions.
 Relatively low residence time avoids alkylate degradation.
 A single driver motor on the mixer simplifies rotary equipment design, cost and maintenance, especially with respect to the seals which, being in the vapor space are less subject to erosion and failure than in the liquid phase Stratco process.
 The reactor can be designed with capacity within the current technology range using one vessel.

The process according to the invention comprises introducing a liquid isoparaffin hydrocarbon reactant/refrigerant with a sulfuric acid alkylation catalyst into the lower end of a generally cylindrical reactor arranged with a substantially vertical longitudinal axis. The reactor also has a sequence of serial reaction zones defined by a plurality of co-acting baffles at vertically spaced intervals that provide an extended reactant flow path in the reactor with the reactants flowing in a sinuous path as they ascend the reactor which promotes vigorous mixing of the reaction mixture as it passes through and up the reactor. Olefin reactant is introduced into the reactant flow path in each of the sequential reaction zones to react with the isoparaffin in the alkylation reaction. With the evolution of the heat of reaction, a portion of the refrigerant reactant is vaporized to effect temperature control in the reactor. Additional mixing and agitation is provided by means of the rotary mixer with its mixing impellers in each of the sequential reaction zones. The vaporized reactant refrigerant and alkylation reaction products leave the reactor at its upper end with the vaporized refrigerant passing to the refrigeration compressor for recycle to the reactor and the alkylation reaction products to the product recovery section of the unit.

DRAWINGS

Figure 2A:
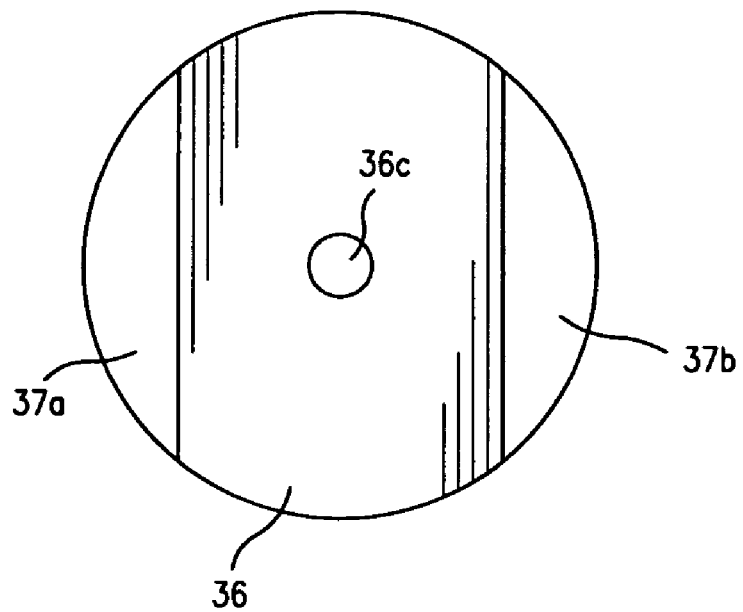
Figure 2B:
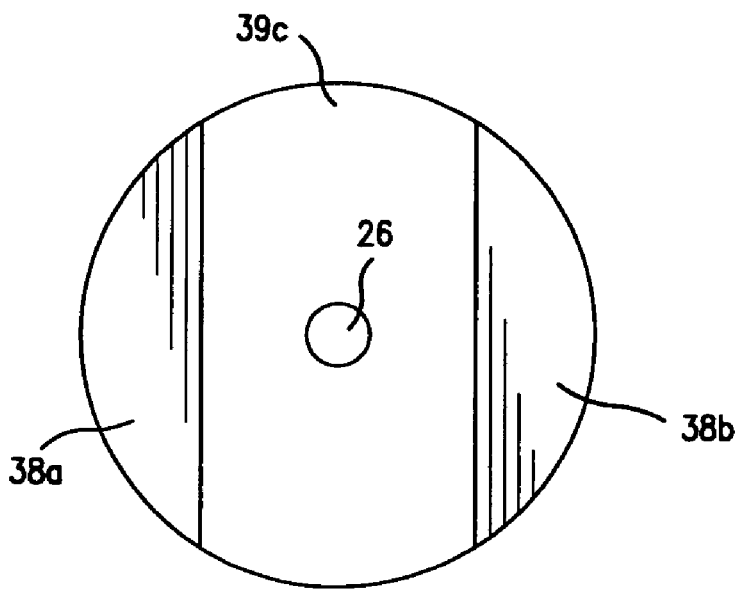

In the accompanying drawings:
 FIG. 1 is a simplified vertical cross section of an autorefrigerant alkylation reactor, and FIGS. 2A and 2B show the configurations of the two types of baffles in the reactor of FIG. 1.

DETAILED DESCRIPTION

The alkylation reactor shown in FIG. 1 has six reaction zones but there are no theoretical limitations on the number of zones that can be provided. The final number of zones will depend on the vessel practical size, hydrodynamic limitations such as coalescing, as well as mixer design but in most cases from four to ten zones will be adequate and convenient. The reactor comprises a vessel 10, cylindrical in form with its central longitudinal axis disposed vertically; the vessel has side wall portion 11 closed at each end by curved lower end plate 12 and a similar upper end plate 13, defining a closed reaction space. An inlet port 15 for refrigerant recycled from the refrigeration system and sulfuric acid alkylation catalyst recycled from the acid settler is provided at the bottom of the vessel located on the axis of the vessel. The refrigerant is fed to inlet port 15 by way of line 16 with the sulfuric acid catalyst entering through line 17, the two being mixed together before passing into the vessel though port 15. The olefin reactant premixed with additional isoparaffin is introduced into the vessel by means of a series (six in number, one in each reaction zone) of spargers 20 supported on feed lines 21 which enter through the side wall 11 of the vessel and deliver the reactants in a uniform pattern in each reaction zone (for clarity only the lowest feed line 21 and its connected sparger 20 are indicated in the lowest reaction zone 35$a$; a similar arrangement is used in each successive reaction zone 35$b$-35$f$ in the reactor). The individual feed lines to each sparger 20 receive incoming reactant by way of line 22. Longitudinal anti-swirl baffles 24 (two shown), which extend vertically along the inside of side wall 11 of the vessel, are added to assist mixing. Four vertical anti-swirl baffles would be adequate.

The isoparaffin comprises one of the feed components for the alkylation reaction and also acts as an autorefrigerant for the process, carrying off heat of reaction by evaporation. Flash zone 25 is located at the bottom of the vessel adjacent inlet 15 and in this zone a portion of the refrigerant isoparaffin evaporates to provide some initial cooling for the charge. The evaporated isoparaffin vapor passes up through the liquid phase in the reactor and besides providing cooling, also agitates the charge in its progress up the vessel. A mixer shaft 26 extends down along the central axis of the vessel, driven by means of motor 27 and journalled in seal/bearing 28. Outlets 29 for the liquid phase reaction mixture are provided proximate the top of vessel 10 in the side wall portion 11 of the vessel below upper end cap 13. Vapor outlets 30 in upper end plate 13 provide a means of egress for vapor, mainly isoparaffin.

The consecutive reaction zones 35$a$-35$f$ are defined by a series of co-acting horizontal baffles located at vertically spaced intervals along the length of the reactor vessel. A primary baffle 36, is mounted in the reactor above flash zone 18 and below the foot of mixer shaft 20 on the vessel axis. This baffle comprises a flat plate having the general configuration shown in FIG. 2A which is fixed to the walls of the reactor at its opposed ends, extending between the walls of the reactor to define two peripheral flow passages 37$a$, 37$b$ through which the mixed acid/refrigerant mixture can pass. The chordal location of the plate edges is selected to provide flow passages adequate to the fluid flow in the reactor. In FIG. 2A, the baffle is shown with a central aperture 36$c$ which is not present in the primary baffle at the bottom of the reaction zones but is present in the similar baffles placed higher up the reactor where these baffles are mounted on the mixer shaft. The horizontal baffles which define the consecutive reaction zones are arranged to provide alternating central and peripheral flow passages for the ascending flow of reactants and refrigerant in the reactor. Baffles 38 have the configuration shown in FIG. 2B with each baffle comprising a pair of plate segments 38a and 38b extending horizontally at the reactor walls and attached to the walls, with a central flow passage 39c defined between the two parallel, chordal edges of the plate segments. As mentioned above, baffles 36 which alternate with baffles 38 have the same general configuration shown in FIG. 2A for the primary baffle plate but also possess a central aperture 36c (not present primary baffle 36) located on the axis of the reactor through which mixer shaft 20 extends; each of these baffles is mounted on the mixer shaft. Thus, each of the six reaction zones 27a-27f in the vessel is defined between successive pairs of baffles in the upward sequence: 36-38-36-38-36-38-36 with the extended, sinuous flow path for the reactant/refrigerant mixture defined between the baffles and by the peripheral flow passages 37a, 37b and central flow passages 39c defined by the baffles alternately along the length of the reactor vessel so that the reaction mixture passes alternately outwards towards the peripheral flow passages and inwardly towards the central flow passages. The alignments of the peripheral segmental flow passages 37a, 37b and the central flow passages 39c may be angularly shifted relative to one another to promote mixing, for example, with the flow passages in the primary baffle located on a 0°-360° alignment and the flow passages in the successive 36 baffles on alignments of 180°-270°, 0°-360°, 180°-270°. Similarly, the central flow passages in baffles 38 may be set on alignments of 0°-360°, 180°-270° and 0°-360°. Other angular displacements may be also used. The cross-sectional areas of the flow passages, both central and peripheral, should be sufficient to allow the desired flow rates up the reactor, making due allowance for the vapor generated by the evaporation of the refrigerant.

Additional mixing of the reactants and catalyst is provided by means of a series of six impellers in the form of paddle blades 40 which are attached to mixer shaft 20 at successive vertically spaced intervals with one paddle blade in each reaction zone between the successive baffle pairs (for clarity only one paddle mixer is designated in the topmost reaction zone 35f, the paddle mixers in the other zones being identical). The longitudinal anti-swirl baffles 24 on the inside of side wall 11 of the vessel co-act with the impellers to assist in the mixing.

As the reaction mixture (isoparaffin/acid catalyst mix initially and then with added olefin/isoparaffin from the spargers) passes upwardly through the reactor vessel, the mixture pursues an extended plug flow path alternately inwards towards the mixer shaft and then outwards away from the shaft towards the vessel walls. In this way, a longer reaction time is provided and good mixing is provided at the points where the olefin reactant is introduced.

The reactants will be the same as those conventionally used in the autorefrigerant process, the light olefin being a $C_2$-$C_6$ olefin, usually propylene or butene and the light isoparaffin a $C_4$-$C_6$ isoparaffin, usually isobutene. The liquid alkylation product will comprises branch-chain paraffins predominantly in the gasoline boiling range, providing a highly suitable gasoline blend component for the refinery. Reaction conditions (temperature, pressure, reactant ratio) will be comparable to those used in the autorefrigerant process.

The invention claimed is:

1. A reactor for the autorefrigerant sulfuric acid isoparaffin/olefin alkylation process which comprises:
    a closed, generally cylindrical reactor vessel with a vertically disposed central axis,
    at least one inlet for refrigerant isoparaffin reactant located at the lower end of the reactor vessel,
    at least one inlet for sulfuric acid catalyst located at the lower end of the reactor vessel,
    at least one outlet for liquid reaction mixture located at the upper end of the reactor vessel,
    at least one vapor outlet located at the upper end of the reactor vessel,
    a series of inlets for olefin reactant at successive vertically spaced intervals up the length of the reactor vessel,
    a series of co-acting baffles having, alternately along the length of the reactor, central flow passages and peripheral flow passages for the reaction mixture to define sequential reaction zones through which the reaction mixture of reactants and sulfuric acid catalyst passes by way of an extended, sinuous flow path,
    a rotary mixer located on the axis of the vessel comprising a driven shaft with multiple impellers to provide agitation to reaction mixture ascending the reactor.

2. A reactor according to claim 1 in which the baffles having peripheral flow passages each comprise a horizontal plate extending horizontally between the walls of the reactor vessel having chordal edges defining peripheral flow passages between the chordal edges and the walls of the reactor vessel.

3. A reactor according to claim 1 in which the baffles having the central flow passages each comprise a plurality of plate segments extending horizontally at the walls of the reactor with a central flow passage defined by chordal edges of the plate segments.

4. A reactor according to claim 3 in which the baffles having the central flow passages each comprise two plate segments extending horizontally at the walls of the reactor with a central flow passage defined by parallel chordal edges of the plate segments.

5. A reactor according to claim 1 in which the inlets for olefin reactant comprise spargers entering the vessel through the side wall of the vessel.

6. A reactor according to claim 1 which comprises a flash zone located at the bottom of the vessel above the inlets for refrigerant isoparaffin reactant and sulfuric acid catalyst.

7. A reactor according to claim 1 which comprises a combines inlet port at the bottom of the vessel to provide inlets for the refrigerant isoparaffin reactant and sulfuric acid catalyst to enter the reactor vessel at one point through the combined inlet port.

* * * * *